United States Patent [19]
Nakamura et al.

[11] Patent Number: 5,858,560
[45] Date of Patent: Jan. 12, 1999

[54] ORGANIC MATERIAL FOR EL DEVICE AND EL DEVICE

[75] Inventors: Norikazu Nakamura; Shinichi Wakabayashi, both of Nagano, Japan

[73] Assignee: Shinko Electric Industries Co., Ltd., Nagano, Japan

[21] Appl. No.: 337,219

[22] Filed: Nov. 7, 1994

[30] Foreign Application Priority Data

Nov. 9, 1993 [JP] Japan ................................. 5-279224

[51] Int. Cl.⁶ .................................................. H05B 33/14
[52] U.S. Cl. ........................ 428/690; 428/917; 428/457; 428/704; 313/502; 313/503; 313/504; 313/506
[58] Field of Search .................................. 428/917, 457, 428/209, 690, 704; 313/502, 503, 504, 506; 252/301.28, 301.32, 301.31, 301.16; 548/219, 94, 113, 224, 179, 236, 414; 564/443

[56] References Cited

U.S. PATENT DOCUMENTS 4,020,081  4/1977  Mackay .................... 548/224
5,149,138  9/1992  Zemsky .................. 252/301.28

FOREIGN PATENT DOCUMENTS 2 442 233  6/1980  France .
2 037 284  7/1980  United Kingdom .

OTHER PUBLICATIONS

Chemistry Letters, No. 9, (1994) 1581–1772.

Kuznetsoua, "Complex compounds of metals with some nitrogen containing ligands", Zhurnal obshchey khimii, vol. XLVI (CVIII), No. 3, Mar. 1976 pp. 670–675.

Hamada et al., "Organic Electroluminescent Devices with 8–Hydroxyquinoline Derivative–Metal Complexes as an Emitter," *Japanese Journal of Applied Physics*, vol. 32, Part 2, No. 4A, Apr. 1, 1993, pp. L514–L515.

Tang et al., "Organic electroluminescent diodes," *Applied Physics Letters*, vol. 51, No. 12, Sep. 21, 1987, pp. 913–915.

Hamada et al., "Blue Electroluminescence in Thin Films of Azomethin–Zinc Complexes," *Japanese Journal of Applied Physics*, vol. 32, Part 2, No. 4A, Apr. 1, 1993, pp. L511–L513.

*Primary Examiner*—Marie Yamnitzky
*Attorney, Agent, or Firm*—Staas & Halsey

[57] ABSTRACT

An organic luminescent material for EL devices comprising a 2-(O-hydroxyphenyl)-benzoxazole or -benzothiazole zinc complex, and an EL device with a luminescent layer containing the material.

4 Claims, 4 Drawing Sheets

ORGANIC MATERIAL FOR EL DEVICE AND EL DEVICE

BACKGROUND OF THE INVENTION

1. Field of the Invention

The present invention relates to organic luminescent materials for EL (electroluminescent) devices and to EL devices, and more particularly it relates to organic luminescent materials for EL devices which exhibit electroluminescence upon the application of a voltage, and to EL devices which employ the above-mentioned organic luminescent materials for EL devices.

2. Description of the Related Art

EL devices employing luminescent materials which exhibit electroluminescence upon the application of a voltage are conventionally used in backlights for displays of OA machines such as word processors and for automobile meters and the like.

Although inorganic luminescent materials have conventionally been used as the luminescent materials for such EL devices, high driving voltages have been required when inorganic luminescent materials for EL devices are caused to emit high-intensity light.

Recently, therefore, research has been conducted in regard to organic luminescent materials for EL devices which allow lower driving voltages (see, for example, C. W. Tang and S. A. VanSlyke: Appl. Phys. Lett. 51. 913 (1987)).

Thin-film EL devices employing such organic luminescent materials make it possible to use lower driving voltages than with EL devices which employ the conventional inorganic luminescent materials for EL devices.

There have also been reported organic luminescent materials which exhibit blue luminescence, and which may be suitably used in backlights for OA machine displays and for automobile meters and the like (see, for example, Jpn. J. Appl. Phys. Vol. 32 (1993) L511).

However, because of the inadequate luminescent intensity of conventional organic luminescent materials exhibiting blue luminescence, organic luminescent materials for EL devices and EL devices have been sought which are capable of blue luminescence of ever higher intensities.

SUMMARY OF THE INVENTION

Here, it is an object of the present invention to provide organic luminescent materials for EL devices which are capable of high-intensity blue or blueish green luminescence, as well as EL devices employing them.

As a result of study aimed at achieving the above-mentioned object, the present inventors have found that an EL device employing a 2-(O-hydroxyphenyl)-benzoxazole or -benzothiazole zinc complex as the luminescent material produces high-intensity blue or blueish green luminescence upon the application of a driving voltage, and thus the present invention has been completed.

In other words, the present invention provides organic luminescent materials for EL devices comprising a 2-(O-hydroxyphenyl)-benzoxazole or -benzothiazole zinc complex represented by the following general formula (I), and EL devices employing the organic luminescent materials.

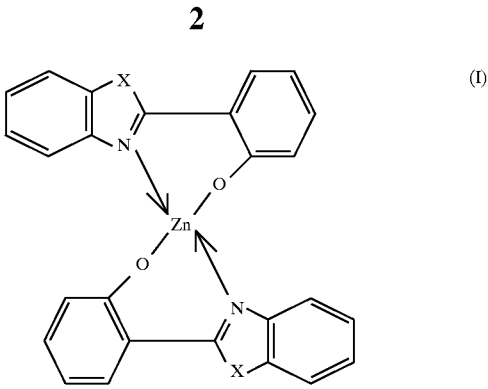

wherein X represents —O— or —S—.

DESCRIPTION OF THE PREFERRED EMBODIMENTS

The organic luminescent material of the present invention is used as a material for the luminescent layer of an EL device. That is, the EL device comprises, in order, an anode layer, a hole injection layer, a luminescent layer and a cathode layer, and according to the present invention the material used as the luminescent layer is an organic luminescent material comprising the zinc complex represented by the above general formula (I). This EL device of the present invention is capable of emitting high-intensity blue or blueish green light when a driving voltage is applied thereto.

The zinc complex of general formula (I) of the present invention may be obtained by, for example, reacting a 2-(O-hydroxyphenyl)-benzoxazole or -benzothiazole represented by the following formula (II) with zinc acetate.

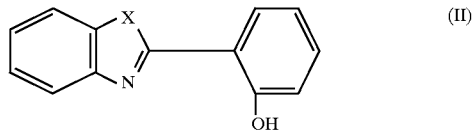

wherein X represents the same species specified previously.

This reaction may be carried out by adding a solution of zinc acetate to a solution of 2-(O-hydroxyphenyl)-benzoxazole or -benzothiazole represented by formula (II) dissolved in a solvent such as methanol, and stirring the mixture at room temperature for a specified period of time.

The reaction product is purified if necessary and then used as the luminescent material for an EL device.

Figure 1:
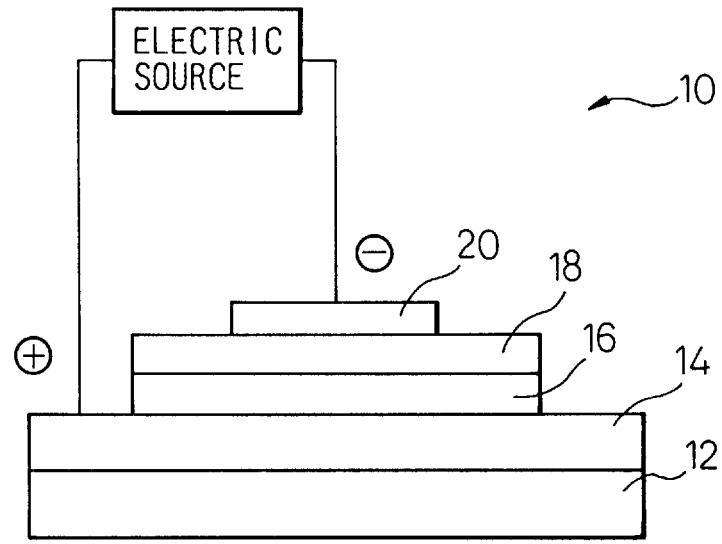
FIG. 1 is a drawing for explanation of an embodiment of an EL device according to the present invention.

The EL device used may have the construction shown, for example, in FIG. 1. The EL device 10 shown in FIG. 1 comprises an ITO transparent electrode (anode) 14 (indium/tin alloy) formed on a transparent glass plate 12, on which are formed in order a hole injection layer 16 composed of a tetraphenyldiamine derivative, a luminescent layer 18 composed of the 2-(O-hydroxyphenyl)-benzoxazole or -benzothiazole zinc complex represented by general formula (I), and an upper electrode 20 composed of a metal such as aluminum.

The hole injection layer 16, luminescent layer 18 and upper electrode 20 may be formed by vacuum deposition. Especially, the hole injection layer 16 and the luminescent layer 18 may be formed by continuous deposition in a high vacuum of about $10^{-6}$ Torr without interrupting the vacuum state.

The anode of this EL device 10 is the ITO transparent electrode 14 and the cathode is the upper electrode 20, and upon the application of a direct current or pulse voltage from a electric source, the luminescent material of the luminescent layer 18 is excited and emits light.

Figure 2:
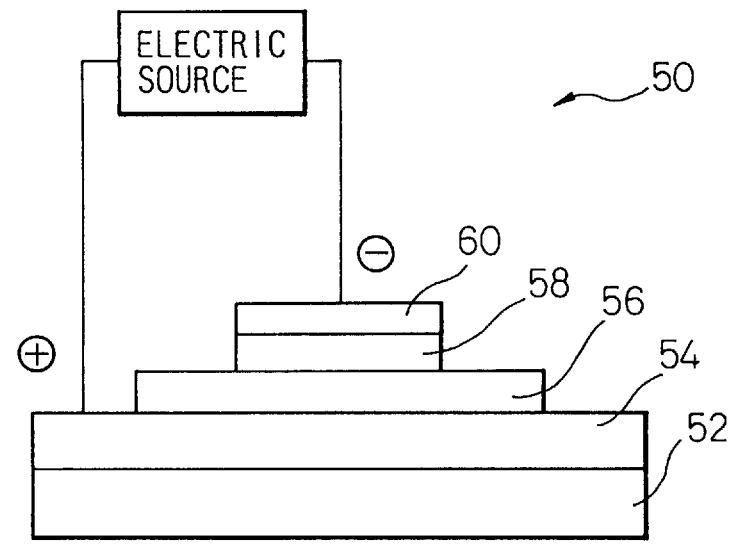
FIG. 2 is a drawing for explanation of another embodiment of an EL device according to the present invention.

The EL device of the present invention may also have the construction shown in FIG. 2. The EL device 50 shown in FIG. 2 comprises an ITO transparent electrode (anode) 54 (indium/tin alloy) formed on a transparent glass plate 52, on which are formed in order a hole injection layer 56 composed of a polycarbonate or other resin, a luminescent layer 58 composed of the 2-(O-hydroxyphenyl)-benzoxazole or -benzothiazole zinc complex represented by general formula (I), and an upper electrode (cathode) 60 composed of a metal such as aluminum.

Here, the hole injection layer 56 may be formed by dissolution of a polycarbonate or other resin in a solvent such as chloroform, followed by dip coating or spin coating, and the luminescent layer 58 and upper electrode 60 may be formed by continuous deposition in a high vacuum of about $10^{-6}$ to $10^{-5}$ Torr without interrupting the vacuum state.

The anode of this EL device 50 is the ITO transparent electrode 54 and the cathode is the upper electrode 60, and upon the application of a direct current or pulse voltage from a electric source, the luminescent layer 58 emits light.

This type of EL device according to the present invention makes it possible to obtain, at low driving voltages, blue luminescence at a higher intensity than with conventional blue light-emitting EL devices. Furthermore, since it is capable of long-term luminescence, it may be suitably used in backlights for displays of OA machines such as computers and for automobile meters and the like.

The present invention will now be explained in more detail with reference to the Examples.

EXAMPLE 1

Synthesis of 2-(O-hydroxyphenyl)benzoxazole zinc complex

A 2.147 g (10.16 mmol) portion of 2-(O-hydroxyphenyl) - benzoxazole was placed in a 300 ml conical flask, 200 ml of methanol was added thereto, and the mixture was stirred while heating at 50° C. to complete dissolution. Also, 1.108 g (5.50 mmol) of zinc acetate dihydrate was placed in a 100 ml conical flask, 10 ml of methanol was added thereto and the mixture was stirred at room temperature to complete dissolution. The methanol solution containing the 2-(O-hydroxyphenyl)benzoxazole was slowly added to the methanol solution containing the zinc acetate, while being kept at 50° C. The mixture was stirred for 3 hours while being heated at 50° C. Combination of the solutions rapidly produced a white precipitate. After 3 hours, the precipitate was filtered out and washed with water, a saturated aqueous solution of sodium bicarbonate, and water, after which it was introduced into 200 ml of water and stirred for one hour while heating at 80° C. The insoluble portion was filtered and introduced into 200 ml of methanol, and then stirred for one hour while heating at 50° C. The insoluble portion was again filtered, washed with methanol and hexane, and then vacuum dried. The yield of the white powder was 2.152 mg (87.8%), and its melting point was 351° C. (DSC measurement).

Figure 3:
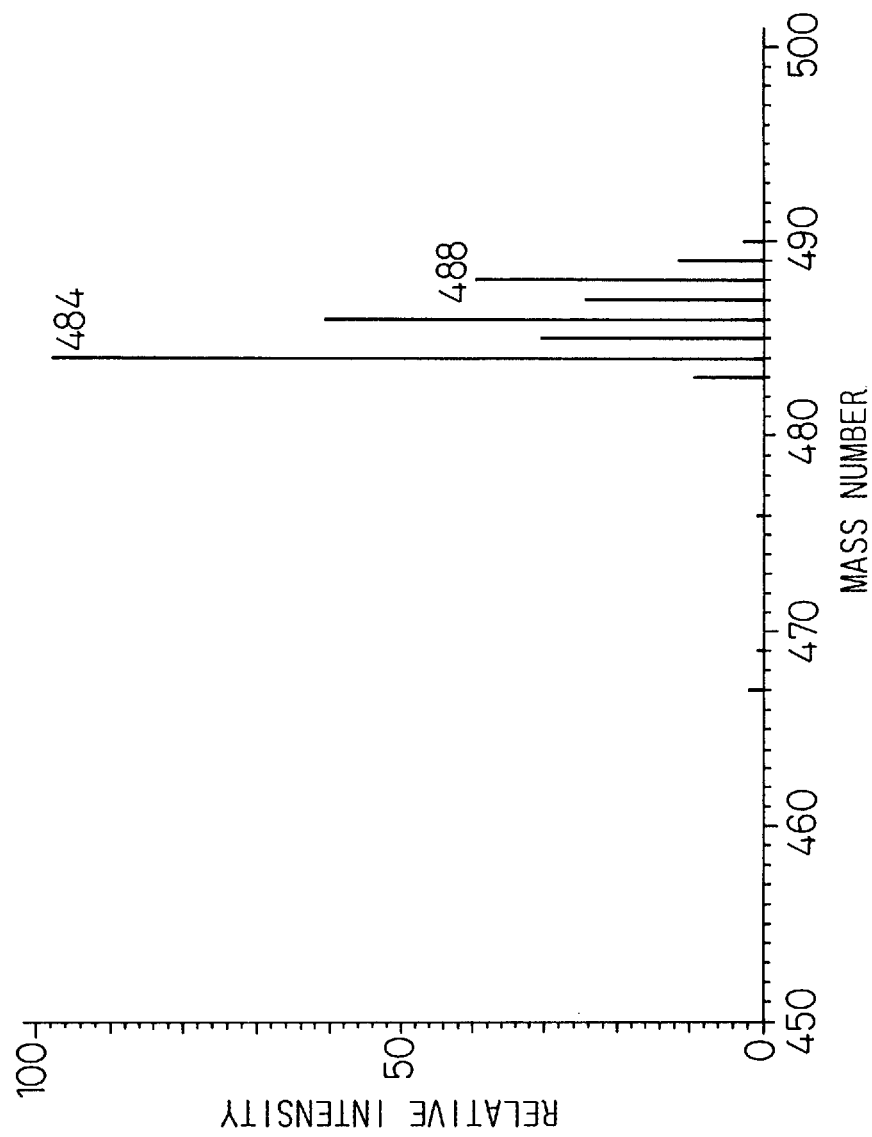
FIG. 3 is a mass spectrogram of a 2-(O-hydroxyphenyl)-benzoxazole zinc complex used in the present invention.

The wavelength of the photoluminescence peak of this zinc complex was 473 nm. Also, upon measurement of the mass spectrum of the complex, the mass spectrogram shown in FIG. 3 was obtained. As shown in FIG. 3, a main peak was observed at a mass number of 484 which is a spectrum specific to the 2-(O-hydroxyphenyl)benzoxazol zinc complex.

Preparation of EL device

The EL device 10 shown in FIG. 1 was prepared by forming in order, on an ITO transparent electrode 14 (indium/tin alloy) having a thickness of about 200 nm formed on a transparent glass plate 12, a hole injection layer 16 having a thickness of about 100 nm and composed of N,N'-diphenyl-N,N'-bis(3-methylphenyl)-[1,1'-biphenyl]-4, 4'-diamine, a luminescent layer 18 having a thickness of about 100 nm and composed of the 2-(O-hydroxyphenyl) benzoxazole zinc complex synthesized earlier, and an upper electrode 20 having a thickness of about 100 nm and composed of a metal such as aluminum.

The hole injection layer 16, luminescent layer 18 and upper electrode 20 were each formed by vacuum deposition. Specifically, the hole injection layer 16 and luminescent layer 18 were both formed by continuous deposition in a high vacuum of about $10^{-6}$ Torr without interrupting the vacuum state. Consequently, the surface areas of the hole injection layer 16 and the luminescent layer 18 were equal.

Luminescence test

Figure 5:
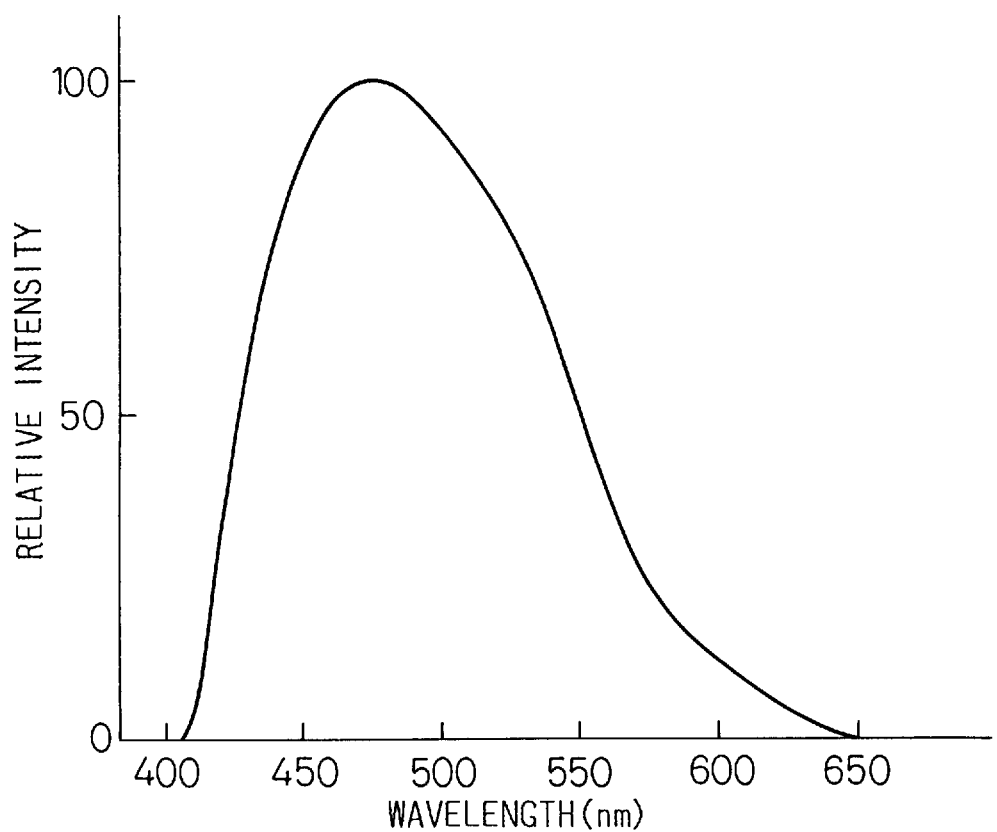
FIG. 5 is an emission spectrogram of the EL device obtained in Example 1.

The anode of the EL device 10 shown in FIG. 1 is the ITO transparent electrode 14 and the cathode is the upper electrode 20, and upon the application of a direct current or pulse voltage of 18 V from a electric source, blue light of an intensity exceeding a few hundred cd/m² was emitted from the luminescent layer 18. The emission spectrum obtained at this time is shown in FIG. 5. The peak wavelength of the device was 475 nm.

In addition, during the continuous luminescence test the emission of blue light was stable and continued for over a few hundred hours.

Comparative Example

An EL device was prepared in the same manner as in Example 1, except that instead of the 2-(O-hydroxyphenyl)-benzoxazole zinc complex used as the luminescent material in Example 1, there was used an azomethine zinc complex represented by the following formula, which is indicated as a blue light-emitting luminescent material in Jpn. J. Appl. Phys. Vol. 32 (1993) L511, cited earlier.

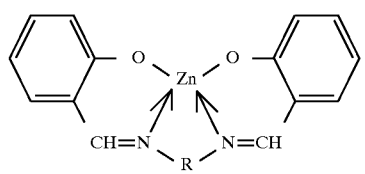

where R represents —$(CH_2)_7$—.

Next, a pulse voltage of 40 Hz, 25 V was applied to the EL device prepared in the Comparative Example and the EL device prepared in Example 1, and visual comparison was made of the degrees of luminescence of both.

As a result, the blue luminescence of the EL device prepared in Example 1 was clearly of higher intensity than the blue luminescence of the EL device prepared in the Comparative Example.

EXAMPLE 2

A luminescence test was conducted in the same manner as in Example 1, except that instead of the EL device 10 of Example 1 having the construction shown in FIG. 1, there was used the EL device 50 having the construction shown in FIG. 2.

The EL device 50 with the construction shown in FIG. 2 was prepared by forming in order, on an ITO transparent electrode 54 (indium/tin alloy) having a thickness of about 200 nm formed on a transparent glass plate 52, a hole injection layer 56 having a thickness of about 100 nm and composed of a polycarbonate resin, a luminescent layer 58 composed of the 2-(O-hydroxyphenyl)benzoxazole zinc complex synthesized in Example 1, and an upper electrode 60 having a thickness of about 100 nm and composed of a metal such as aluminum.

The hole injection layer 56 was formed by dissolution of the polycarbonate resin in chloroform, followed by dip coating or spin coating, and the luminescent layer 58 and upper electrode 60 were formed by continuous deposition in a high vacuum of about $10^{-6}$ to $10^{-5}$ Torr without interrupting the vacuum state. Consequently, the surface areas of the luminescent layer 58 and the upper electrode 60 were equal.

For the luminescence test of the obtained EL device 50, the anode was the ITO transparent electrode 54 and the cathode was the upper electrode 60, and upon the application of a direct current or pulse voltage of 18 V from a electric source, blue light of an intensity exceeding 1000 cd/m² was emitted from the luminescent layer 58. In addition, during the continuous luminescence test the emission of blue light was stable and continued for over a few hundred hours.

EXAMPLE 3

Synthesis of 2-(O-hydroxyphenyl)benzothiazole zinc complex

A 484 mg (2.13 mmol) portion of 2-(O-hydroxyphenyl)-benzothiazole was placed in a 100 ml conical flask, 40 ml of methanol was added thereto, and the mixture was stirred while heating at 50° C. to complete dissolution. Also, 226 mg (1.03 mmol) of zinc acetate dihydrate was placed in a 50 ml conical flask, 20 ml of methanol was added thereto and the mixture was stirred while heating at 50° C. to complete dissolution. The methanol solution containing the 2-(O-hydroxyphenyl)-benzothiazole was slowly added to the methanol solution containing the zinc acetate, while being kept at 50° C. Combination of the solutions rapidly produced a green precipitate, and this mixture was further stirred for 1 hour and 45 minutes while heating at 50° C. The precipitate was filtered out and washed with water, a saturated aqueous solution of sodium bicarbonate, water, methanol and hexane, and then vacuum dried. The yield of the green powder was 316 mg (59%), and its melting point was 304° C. (DSC measurement).

Figure 4:
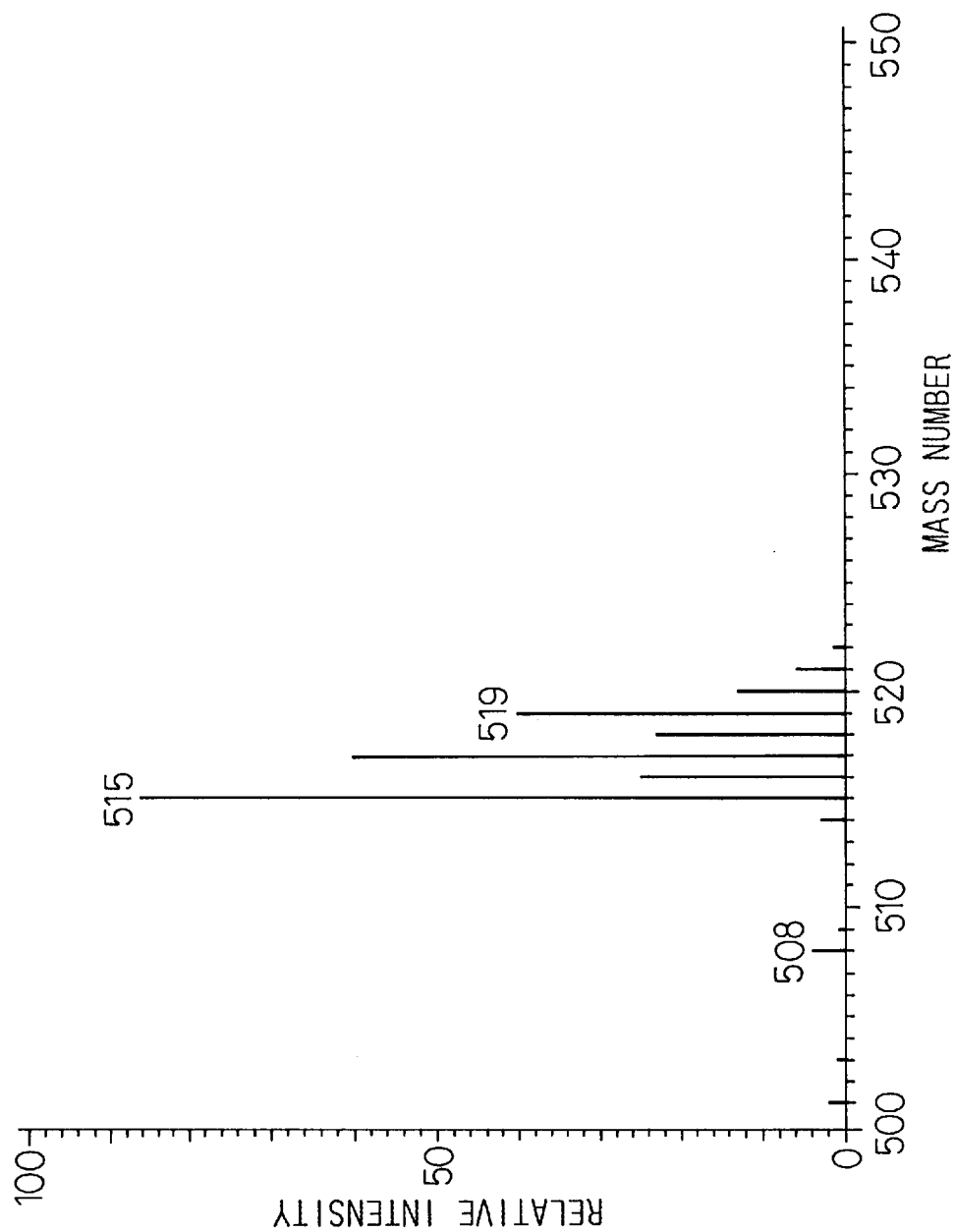
FIG. 4 is a mass spectrogram of a 2-(O-hydroxyphenyl)-benzothiazole zinc complex used in the present invention.

The wavelength of the photoluminescence peak of this zinc complex was 500 nm. Also, upon measurement of the mass spectrum of the complex, the mass spectrogram shown in FIG. 4 was obtained. As shown in FIG. 4, a main peak was observed at a mass number of 515 which is a spectrum specific to the 2-(O-hydroxyphenyl)benzothiazol zinc complex.

Preparation of EL device

The EL device 10 shown in FIG. 1 was prepared by forming in order, on an ITO transparent electrode 14 (indium/tin alloy) of a thickness of about 200 nm formed on a transparent glass plate 12, a hole injection layer 16 of a thickness of about 100 nm composed of N,N'-diphenyl-N, N'-bis(3-methylphenyl)-[1,1'-biphenyl]-4,4'-diamine, a luminescent layer 18 of a thickness of about 100 nm composed of the 2-(O-hydroxyphenyl)-benzothiazole zinc complex synthesized earlier, and an upper electrode 20 of a thickness of about 100 nm composed of a metal such as aluminum.

The hole injection layer 16, luminescent layer 18 and upper electrode 20 were each formed by vacuum deposition. Specifically, the hole injection layer 16 and luminescent layer 18 were both formed by continuous deposition in a high vacuum of about $10^{-6}$ Torr without interrupting the vacuum state. Consequently, the surface areas of the hole injection layer 16 and the luminescent layer 18 were equal.

Luminescence test

The anode of the EL device 10 shown in FIG. 1 is the ITO transparent electrode 14 and the cathode is the upper electrode 20, and upon the application of a direct current or pulse voltage of 18 V from a electric source, blueish green light of an intensity exceeding a few hundred cd/m² was emitted from the luminescent layer 18.

In addition, during the continuous luminescence test the emission of blueish green was stable and continued for over a few hundred hours.

We claim:

1. An EL device which includes in order, an anode layer, a hole injection layer, a luminescent layer and a cathode layer, wherein said luminescent layer comprises a zinc complex represented by the following formula (I):

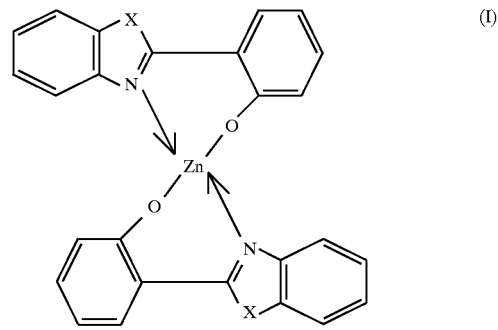

wherein X represents —O—, and
wherein the zinc complex of general formula (I) is 2-(O-hydroxyphenyl)benzoxazole zinc complex.

2. An EL device according to claim 1, wherein said hole injection layer includes a tetraphenyldiamine derivative.

3. An EL device according to claim 1, wherein said hole injection layer includes a polycarbonate resin.

4. An EL device according to claim 1, wherein said anode layer is an ITO transparent electrode.

* * * * *